United States Patent

Haeckel et al.

(10) Patent No.: US 9,133,944 B2
(45) Date of Patent: Sep. 15, 2015

(54) SWITCHING VALVE TO CONTROL A FLUID SUBJECT TO HIGH PRESSURE

(71) Applicants: Michael Haeckel, Germering (DE); Richard Schloderer, Krailling (DE)

(72) Inventors: Michael Haeckel, Germering (DE); Richard Schloderer, Krailling (DE)

(73) Assignee: DIONEX SOFTRON GMBH, Germering (DE)

( * ) Notice: Subject to any disclaimer, the term of this patent is extended or adjusted under 35 U.S.C. 154(b) by 154 days.

(21) Appl. No.: 13/705,657

(22) Filed: Dec. 5, 2012

(65) Prior Publication Data

US 2013/0139913 A1 Jun. 6, 2013

(30) Foreign Application Priority Data

Dec. 6, 2011 (DE) .......................... 10 2011 056 094

(51) Int. Cl.
*F16K 15/04* (2006.01)
*F16K 27/02* (2006.01)
*F04B 53/10* (2006.01)
*F16K 25/00* (2006.01)
*G01N 30/32* (2006.01)

(52) U.S. Cl.
CPC ........... *F16K 15/042* (2013.01); *F04B 53/1005* (2013.01); *F16K 25/005* (2013.01); *F16K 27/0245* (2013.01); *G01N 2030/328* (2013.01); *Y10T 137/7838* (2015.04); *Y10T 137/791* (2015.04)

(58) Field of Classification Search
CPC . F16K 15/042; F16K 27/0245; F16K 25/005; Y10T 137/791; Y10T 137/7838; F04B 53/1005; G01N 2030/328
USPC ........ 137/512, 454.6, 533.11, 512.1; 251/368
See application file for complete search history.

(56) References Cited

U.S. PATENT DOCUMENTS

| 3,174,437 | A | * | 3/1965 | Street .......................... 417/554 |
| 3,444,884 | A | | 5/1969 | Huddle |
| 4,139,469 | A | * | 2/1979 | Rainin et al. ................. 210/136 |
| 4,781,213 | A | | 11/1988 | Kilayko |
| 4,832,075 | A | * | 5/1989 | Dubach ........................ 137/512 |
| 4,846,218 | A | | 7/1989 | Upchurch |
| 4,862,907 | A | | 9/1989 | Ledtje et al. |

(Continued)

FOREIGN PATENT DOCUMENTS

DE   202006018959 U1 *  3/2007
DE   102008042252         4/2009

(Continued)

*Primary Examiner* — Craig Schneider
*Assistant Examiner* — David Colon Morales
(74) *Attorney, Agent, or Firm* — Timothy J. Ohara

(57) ABSTRACT

A switching valve, in particular for controlling a fluid subject to high pressure is described. The switching valve has at least one valve unit, which includes a valve seat element and a switching element guided movably in a guide element, wherein the valve seat element and the switching element interact to provide a switching valve function. The valve seat element and the guide element are provided in a housing. The valve seat element, the guide element and the housing form a through flow channel for the fluid to be controlled. An elastically and/or plastically deformable sealing body is provided in a fully enclosed space between the inner wall of the housing and the outer walls of the valve seat element and of the guide element. The sealing body can be subject to a predetermined pressure to seal off the through flow channel from the housing and subject the valve seat element and the guide element to an inward-directed preload.

19 Claims, 1 Drawing Sheet

(56) References Cited

U.S. PATENT DOCUMENTS

| | | | |
|---|---|---|---|
| 4,945,945 A | 8/1990 | Schmid | |
| 4,974,628 A * | 12/1990 | Tepermeister et al. | 137/454.4 |
| 5,002,662 A * | 3/1991 | Ledtje et al. | 210/198.2 |
| 6,273,124 B1 * | 8/2001 | Huber et al. | 137/362 |
| 2005/0173468 A1 | 8/2005 | Matsumoto et al. | |
| 2008/0020136 A1 * | 1/2008 | Ciolkosz et al. | 427/208.4 |
| 2008/0136122 A1 * | 6/2008 | Gambier | 277/650 |
| 2010/0175206 A1 | 7/2010 | Sauer et al. | |
| 2011/0094954 A1 | 4/2011 | Wagner | |

FOREIGN PATENT DOCUMENTS

| | | |
|---|---|---|
| DE | 102008042252 A1 | 4/2009 |
| EP | 1514027 B1 | 12/2011 |

\* cited by examiner

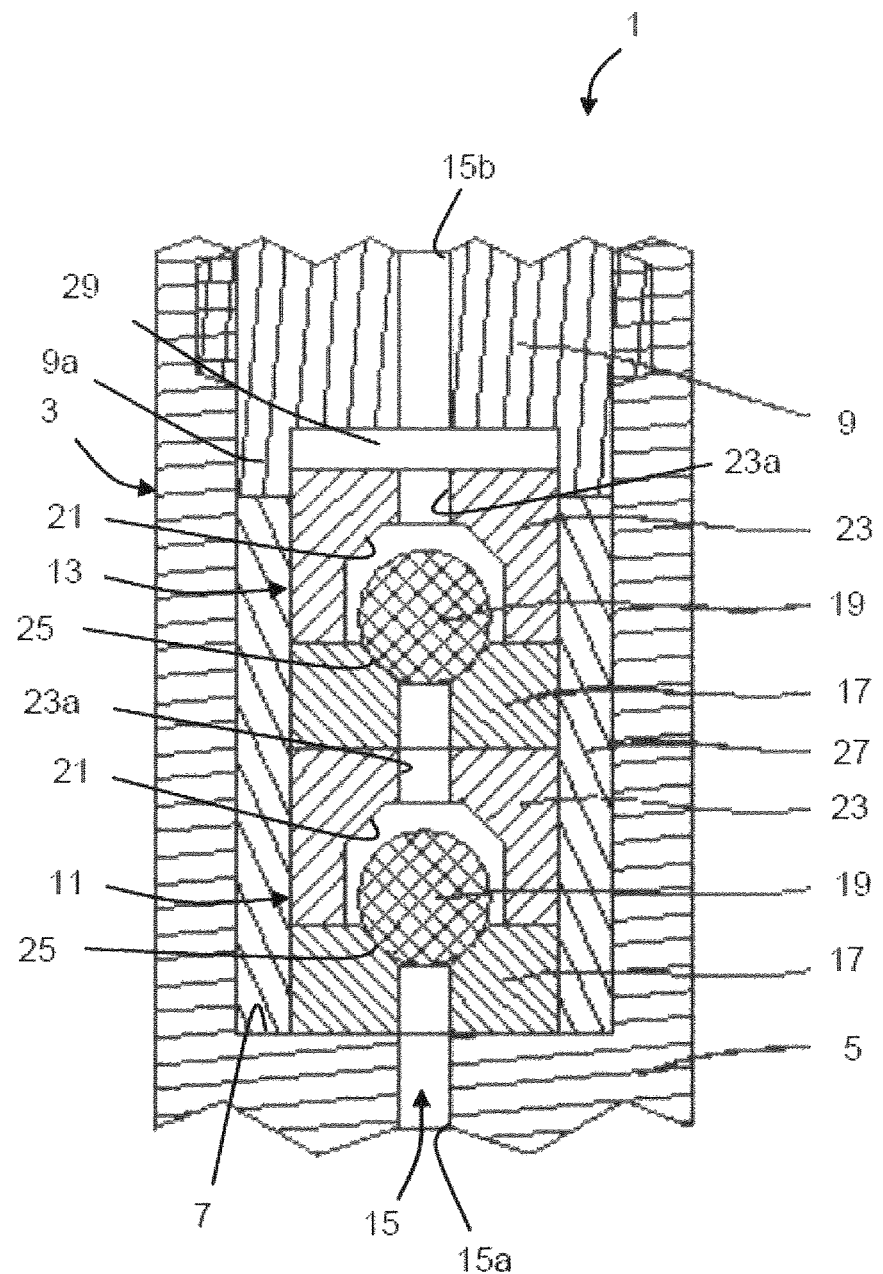

SWITCHING VALVE TO CONTROL A FLUID SUBJECT TO HIGH PRESSURE

FIELD OF THE INVENTION

The invention relates to a switching valve, in particular to control a fluid subject to high pressure.

BACKGROUND

In liquid chromatography, especially in high performance liquid chromatography (HPLC), substances are separated by being flushed through a chromatography column at high pressure with the aid of a solvent. To produce the liquid flow required for this purpose, there is a need for pumps capable of continuously supplying what is usually a very low, constant flow rate at high pressure. In order to achieve more rapid separation or separation with better resolution in HPLC, ever higher pressures have been used in recent years.

To produce the liquid pressure, piston pumps are usually used in HPLC. These pumps generally employ passive check valves at the inlet and at the outlet, these valves usually being designed as ball valves. Check valves of this kind switch from a CLOSED state to an OPEN state and vice versa in accordance with the direction of the applied pressure difference of the fluid flow to be controlled, said difference being applied across the valve (or the switching element concerned), or in accordance with the direction of the fluid flow through the through flow channel of the valve. The valves each contain a valve seat, a switching element designed as a ball and a guide element for guiding the switching movement of the switching element. The valve seat element and the switching element must each consist of a very hard and yet tough material in order to allow a sufficiently high surface pressure in the CLOSED state for the high pressures to be controlled. The switching element designed as a ball often consists of ruby and the valve seat often consists of sapphire. However, ceramic materials, such as $AlO_2$ or $ZrO_2$, are also suitable for producing these elements, for example. These materials have the advantage that they are very hard and strong in compression. This is necessary because extremely high pressures occur locally in the region of the sealing surface, i.e. the contact surface between the valve seat element and the switching element, and these can amount to a multiple of the liquid pressure.

In order to increase the reliability of a check valve of this kind, two (or even more) full valves or valve units arranged in a common housing can be connected in series to form a dual check valve. For correct operation, it is therefore sufficient if one of the two valves or one of the two valve units is still intact, in particular leaktight in the CLOSED state.

For correct operation of a check valve, it is necessary to seal off the elements of a valve unit, in particular, the valve seat element and the switching element guided movably in a guide element, in such a way that no liquid can pass through the check valve or the valve unit concerned in the CLOSED state due to leaks. For this purpose, the individual components of the valve must be sealed off relative to one another and relative to the housing accommodating them. This sealing must withstand alternating loads up to the maximum pressure of the pump on a sustained basis.

Ruby, sapphire and ceramic are very strong in compression but withstand only a relatively low tensile stress. Since the valve seat element and also the guide element for the switching element generally have a (usually axial) opening for the passage of the fluid flow to be controlled and, consequently, the fluid pressure acts on the inner walls of said elements, (primarily azimuthal or tangential) tensile stresses arise during a deformation of the walls of said elements, possibly leading to fracture of the material. The pressure of the ball on the valve seat, which is formed by a switching element or ball contact surface extending obliquely to the axis of the through opening for the fluid, can also lead to fracture of the seat element due to the resulting (predominantly azimuthal) tensile stresses.

In known check valves, there are various known possibilities for sealing off the components relative to one another and relative to the housing (in other words for sealing off the through flow channel defined by the components).

In general, all the components of a valve unit, in particular the valve seat element and the guide element together with the switching element accommodated therein, are installed in a metal sleeve. Caps made of PEEK are used at the two ends of the sleeve in order to seal off the entire unit. It is also possible for two valve units to be arranged in the metal sleeve and, in this case, the use of a further, thin sealing washer made of PEEK between the two valve units of the dual check valve is known. This design is reliable up to pressures of about 1000 bar. At higher pressures, however, there is the problem that the caps are subject to excessive plastic deformation in continuous use and begin to leak over time.

Another possibility is to use thin PEEK washers or metal washers at the ends as well, as is the case with the valves illustrated in EP 1 514 027 B1. However, only sealing at the ends is possible with such washers, and this requires a complex design in the case of a dual ball valve. Moreover, high demands are made of the quality and structure of the surface. In EP 1 514 027 B1, for example, concentric grooves are proposed.

For the problem of the limited stability of the seat and the guide element due to the occurrence of tensile stresses, one known practice is to make the contact surface between the valve seat and the guide element for the ball with a controlled leakage in order to allow a pressure equalization between the inside and the outside. The sealing between the two individual valves of the dual ball valve must then be such that this region is also leaktight with respect to the sleeve.

Another known practice is to press fit the valve seat elements into a metal ring and thereby subject them to a radially inward load. The disadvantage of this variant consists in the additional production outlay associated therewith.

Finally, there is the possibility of producing the guide element for the switching element, not from ceramic, but from stainless steel, which has a higher tensile strength. However, the stability problem of the valve seat element cannot be solved in this way since stainless steel is not a suitable material for the valve seat (or for the switching element).

U.S. 2011/0094954 A1 discloses the practice of making the valve seats conical at the outer circumference and preloading them in the axial direction by means of complementary mating parts. A preload with a radially inward component is thereby also produced, and this is capable of absorbing some of the expansion of the annular seat element caused by the fluid pressure. However, this variant requires an increased production outlay and an increased number of components with complex contours, especially in the case of a dual ball valve.

SUMMARY

A switching valve to control a fluid subject to high pressure is described. The switching valve includes at least one valve unit and an elastically and/or plastically deformable sealing body. The at least one valve unit includes a valve seat element and a switching element guided movably in a guide element, wherein the valve seat element and the switching element interact to provide a switching valve function. The valve seat element and the guide element are provided in a housing and wherein the valve seat element, the guide element and the housing form a through flow channel for the fluid to be controlled. The elastically and/or plastically deformable sealing body can be provided in a fully enclosed space between an inner wall of the housing and an outer walls of the valve seat element and of the guide element. The sealing body can be subjected to a predetermined pressure and thus seals off the through flow channel and subjects the valve seat element and the guide element to an inward-directed preload pressure.

In regards to the above switching valve, the pressure in the sealing body can be greater than a maximum pressure of the fluid to be controlled in the through flow channel.

In regards to the above switching valve, the housing may be of at least a two-part design, in that a receiving recess for the valve seat element, the guide element and the sealing body is provided in a first housing part, and in that a second housing part is connected to the first housing part that subjects the sealing body to the predetermined pressure.

In regards to the above switching valve, the receiving recess in the first housing part may be cylindrical, and in that the valve seat element and the guide element have an axially flush cylindrical outer wall.

In regards to the above switching valve, the second housing part can be connected detachably to the first housing part by screwing, and in that the second housing part has an annular extension, which engages in an annular space that subjects the sealing body to the predetermined pressure and closes the space.

In regards to the above switching valve, the guide element can have a recess to receive the switching element, in which the recess is configured so that an axial movement of the switching element into an OPEN position of the valve, which takes place in a direction away from the valve seat, is limited.

In regards to the above switching valve, starting from an initial state after an introduction and closure of the fully enclosed space, a volume of the fully enclosed space can be reduced to such an extent by a plastic deformation of that region of the housing which surrounds the fully enclosed space that the predetermined pressure is achieved within the sealing body.

In regards to the above switching valve, the sealing body can surround at least one further valve unit, which is in alignment with the first valve unit and which forms at least one further through flow channel that is connected fluidically in series with the through flow channel of the first valve unit.

In regards to the above switching valve, the at least one further valve unit can be of identical design to the first valve unit and in that the valve units are in direct axial contact with one another.

In regards to the above switching valve, the switching element may be a material selected from ruby, sapphire, or ceramic material such as $AlO_2$ or $ZrO_2$. Similarly, the valve seat element may also be a material selected from ruby, sapphire, $AlO_2$ ceramic or $ZrO_2$ ceramics. The housing may include a metallic material selected from stainless steel or titanium alloy. The sealing body can include a thermoplastic such as, for example, a polyether ether ketone (PEEK).

In regards to the above switching valve, the valve can be configured to be a check valve in which the switching element is a ball.

In regards to the above switching valve, an outer wall of the housing can be configured to be elastically or plastically deformable in at least one partial region to delimit the fully enclosed space when above a predetermined pressure whereby the pressure in the sealing body is held constant or a rise in pressure is reduced, a size of the fully enclosed space in a region of impingement is reduced, and that a deformation of the wall of the housing keeps a total volume of the fully enclosed space substantially constant or that a reduction in the total volume is less than a reduction in volume in the region of impingement.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1 shows a schematic cross section of a switching valve in the form of a ball check valve.

DETAILED DESCRIPTION OF EMBODIMENTS

A switching valve to control a fluid subject to high pressure is described that has a simple design and a small number of components, which ensures a long service life and switching endurance, and a high level of reliability and leaktightness, even at extremely high pressures.

The invention proceeds from the insight that the provision of a sealing body capable of elastic and/or plastic deformation in a fully enclosed space provided around the valve unit means that the components of the valve unit can be sealed off from one another and from the housing in which the valve unit is accommodated in an extremely simple manner if the sealing body is subjected to a predetermined pressure in the fully enclosed space. As a result, the sealing body is deformed and flows into any small opening to be closed. To achieve this, the material of the sealing body must, of course, be chosen in such a way that it has sufficient structural strength to prevent it from itself flowing through the small openings to be sealed off and, in the process, becoming detached from the body so that the latter is destroyed and, ultimately, the pressure in the fully enclosed space is also reduced through a loss of material. Of course, the maximum permissible size of the locations to be sealed off in the fully enclosed space must be matched to the material of the sealing body and, conversely, the material must be matched to the size of the locations to be sealed off.

At the same time, the sealing body under pressure makes possible a radially inward preload on the enclosed components of the valve unit, in particular the valve seat element but also the guide element for the switching element. In this respect, the sealing body acts virtually as a solid-body hydraulic medium, which can be acted upon at any location during assembly in such a way that a virtually uniform pressure is obtained in the volume of the sealing body, said pressure acting on the outer walls of the enclosed components of the valve unit. Because of the compressibility of the material of the sealing body and the presence of small gaps between the sealing element and the surrounding components, a reduction in the volume of the fully enclosed space is required to produce a sufficiently high pressure within the material.

According to a preferred embodiment, the selected pressure in the sealing body is greater than the maximum pressure of the fluid to be controlled in the through flow channel.

According to one embodiment, the housing can be of at least two-part design, wherein a receiving recess for the valve seat element, the guide element and the sealing body is provided in a first housing part, and wherein a second housing part is connected to the first housing part, acting upon the sealing element, during the assembly of the valve, at that end of the fully enclosed space which faces it, it being possible in this case for said space to be designed as an annular space, so as to produce the desired pressure in the sealing body.

The receiving recess in the first housing part can be of cylindrical design, preferably of circular-cylindrical design. The same also applies to the valve seat element and the guide element, which can have a preferably axially flush cylindrical outer wall. If both the receiving recess and the valve unit consisting of the valve seat element and the guide element (with the switching element provided therein) are of circular-cylindrical cross section, a circular-cylindrical annular space is obtained, which can be filled by the sealing body, the latter having a correspondingly simple shape.

In order to close off the fully enclosed space at the relevant end and to produce the pressure in the sealing body, the second housing part can be connected detachably to the first housing part, preferably by screwing. For this purpose, the second housing part can have an annular extension, which engages in the fully enclosed space, closes the latter and acts upon the sealing body. By means of a corresponding thread on the first and second housing parts, the desired pressure in the housing or in the sealing body can be achieved without problems and without exerting a large force and, if required, can also be finely adjusted.

According to one embodiment, the guide element can have a recess for receiving the switching element, which recess is configured in such a way that the axial movement of the switching element into an open position of the valve, which takes place in a direction away from the valve seat, is limited. For this purpose, the guide element can have an opening on the side remote from the valve seat in the relevant wall of the guide element for the passage of the fluid, wherein the inner wall facing the switching element is designed in such a way that a sufficiently large opening remains for the passage of the fluid, even when the switching element is in contact.

During the assembly of the switching valve, starting from an initial state after the introduction and closure of the space, the volume of the fully enclosed space can be reduced to such an extent by a plastic deformation of that region of the housing which surrounds the space that the predetermined pressure is achieved within the sealing body.

The switching valve can also be designed as a dual valve or a multiple valve. In such embodiments, the sealing body can surround at least one further valve unit, which is in alignment with the first valve unit and which forms a through flow channel that is connected fluidically in series with the through flow channel of the first valve unit.

The at least one further valve unit can be of identical design to the first valve unit. In this arrangement, the two valve units can be in direct axial contact with one another, with the result that the sealing body, which also surrounds the joint between the two valve units, can also seal off said joint. At the same time, fixing in the axial direction can be accomplished by the radial action on the outer walls of the two valve units.

However, it is, of course, also possible for the at least one valve unit to be additionally fixed in the axial direction within the receiving recess of the housing, preferably even before the outer wall is subjected to pressure in the radial direction by the sealing body, in order to avoid a situation where the valve units and the components concerned move apart axially. The reason is that in this way such large gaps might be formed between the axially adjacent components of the at least one valve unit that they could no longer be reliably closed by the sealing body and/or would lead to destruction of the sealing body.

As already explained above, the switching element can be designed as a ball, leading to a very simple valve design.

The switching element or the valve seat element can consist of a hard material, preferably of ruby, sapphire or a ceramic material, such as $AlO_2$ or $ZrO_2$.

The housing of the valve can consist of a metallic material of sufficient tensile strength, preferably of stainless steel or of a titanium alloy.

Suitable materials for the sealing body include, in particular, thermoplastics, preferably a polyether ether ketone (PEEK). However, it is also possible, for example, to use a polyethylene (PE) or polytetrafluoroethylene (PTFE) material.

According to one embodiment, the choice of material and/or geometrical configuration means that the outer wall of the housing of the valve is elastically or plastically deformable to such an extent, in at least one partial region, in which it delimits the fully enclosed space, that, above a predetermined pressure in the sealing body, the pressure is held constant or the rise in pressure is reduced, despite a further reduction in the size of the fully enclosed space in a region of impingement, by virtue of the fact that the deformation of the wall keeps the total volume of the fully enclosed space substantially constant or that the reduction in the total volume is less than the reduction in volume in the region of impingement.

In the case of a two-part housing, it is thereby possible to ensure that tolerances in the production of the valve components do not lead to an impermissibly high pressure in the sealing body during the assembly of the valve, especially in the case of embodiments in which the second housing part is used to fix further valve components in the housing and, accordingly, must be connected to the first housing part in a particular position during assembly.

Further embodiments of the invention will be apparent from the dependent claims. The invention is explained in greater detail below with reference to an illustrative embodiment shown in the drawing.

FIG. 1 shows a schematic cross section through an embodiment of a switching valve in the form of a ball check valve.

The check valve 1 illustrated in FIG. 1 in a schematic longitudinal section can be embodied as a separate constructional unit or can be integrated into some other, overall unit (not shown specifically), such as a pump. The check valve 1 includes a housing 3, which can be of two- or multi-part design. If the valve 1 is integrated into another subassembly, the housing 3 can, of course, also be integrated with a housing or some other component of the other subassembly. In particular, the housing 3 can be integrated with the pump head or the relevant housing or main body of the pump head of an HPLC pump.

In the illustrative embodiment shown in FIG. 1, the housing 3 includes a first housing part 5, which has a cylindrical receiving recess 7, in which the other components of the check valve are accommodated, and a second housing part 9, which is connected to the first housing part 5 and closes the opening of the receiving recess 7 in a leaktight manner. For this purpose, it is possible, as in the embodiment illustrated in FIG. 1, for respective threads to be provided in an upper region of the inner wall of the receiving recess 7 and in a region of the outer wall of the second housing part 9, which is likewise of cylindrical design, at least in the region which engages in the receiving recess 7. The two threads permit a detachable connection between the first and second housing parts 5, 9. However, other detachable or non-detachable joints are, of course, also possible between the two housing parts 5, 9, e.g. those provided by welding, soldering, adhesive bonding or crimping.

In regards to the other components of the valve 1 which are accommodated in the receiving recess 7, these are a first valve unit 11 and a second valve unit 13, which are of identical design.

The housing 3 and the valve units 11, 13 define a through flow channel 15 with a feed opening 15a in the bottom of the first housing part 5 and an outlet opening 15b for the fluid to be controlled in the second housing part 9. The check valve illustrated in FIG. 1 provides a single path for the fluid. In the case of a multi-way switching valve, to which the principle of the invention can likewise be applied, there can also be a plurality of connected paths. For example, the valve can be configured in such a way that an incoming fluid flow is switched selectively to one of a plurality of further paths.

The fundamental components of the valve units 11, 13 of the ball check valve illustrated in FIG. 1 are in each case a valve seat element 17 and a switching element in the form of a ball 19, which is accommodated in a manner which allows substantially axial movement in a guide recess 21 of a guide element 23. The valve seat element of each of the valve units 11, 13 is of substantially annular design and, at the coaxial opening, has a seat surface 25 which is of complementary design to the outer surface of the ball 19 in order to ensure sealing in a CLOSED operating position of the valve 1.

In the case of the ball check valve illustrated, the CLOSED operating position is reached when the pressure of the fluid in the through flow channel 15 in regions above the balls 19 or in regions beyond the seat surfaces 25 (i.e. in the direction of the outlet opening 15b) is greater than in regions below the seat surfaces (i.e. in the direction of the feed opening 15a). The OPEN operating position is assumed when the pressure conditions are reversed, wherein the balls 19 are moved by the resulting fluid flow in the direction of flow, i.e. in the direction of the outlet opening 15b, until they strike against the bottom of the guide recess 21 of the respective guide element 23.

The guide elements 23 are of cup-shaped design and, in the bottom, have a through opening 23a for the passage of the fluid. The guide element 23 configured in this way ensures that the ball 19 cannot move too far out of the CLOSED operating position and the fitting of further components (in the direction of through flow) is possible. On the inside, the bottom is designed in such a way that it is not rotationally symmetrical in the region of the through opening 23a, thus ensuring that the ball 19 is limited in its stroke but cannot close the outlet opening 23a.

The seat element 17 of the valve units 11, 13 can consist of sapphire, and the ball 19 can consist of ruby, for example. $AlO_2$ and $ZrO_2$ ceramic materials can likewise be used for these components. The guide element 23 of the valve units 11, 13 can consist of an $AlO_2$ ceramic, for example.

The dual arrangement of the ball check valve units 11, 13 increases the fail safety of the valve 1. If one valve unit 11, 13 begins to leak, the other valve unit 13, 11 continues to maintain the leaktightness of the valve.

As illustrated in FIG. 1, the valve seat elements 17 and the guide elements 23 have respective outer contours which are substantially in alignment in the axial direction. A sealing body 27 is arranged between the components of the valve units 11, 13 that are arranged in the receiving recess 7 and the inner wall of the receiving recess 7, i.e. in the annular space concerned. The sealing body 27 preferably has a complementary (in this case sleeve-shaped) configuration, even in the unpressurized state. The axial overall length of the sealing body 27 preferably corresponds approximately to the axial extent of the two valve units 11, 13. However, at least the overall length and the position of the sealing body 27 should be such that all the openings and gaps (see below) to be sealed off are covered by the sealing body 27 (and the annular space around the sealing body 27 is closed).

At this point, it should be noted that the term "annular space" in the present description is used in a very general sense for a space which lies between an outer wall of any desired shape and an inner wall of any desired shape and which can be closed at the bottom and at the top to form a fully enclosed annular space.

To assemble the valve, a unit consisting of the valve units 11, 13 and the sleeve of the sealing body 27, said sleeve being slipped over the valve units, can first of all be produced. The overall unit can then be inserted into the receiving recess 7 of the first housing part 5. The second housing part 9 can then be connected to the first housing part 5 from above (being screwed in the embodiment illustrated).

On the region that engages in the receiving recess 7, the second housing part 9 has an annular extension 9a, which engages in the upper region of the annular space between the valve unit 13 and the receiving recess 7 and substantially closes said recess (apart from a permissible gap). The annular space in which the sealing body 27 is accommodated is thus fully enclosed (apart from permissible gaps).

The annular extension 9a of the second housing part 9 is inserted into the receiving recess 7 of the first housing part until the sealing body 27 is subjected to a predetermined pressure. Under this pressure, the plastically and/or elastically deformable material of the sealing body 27 is deformed and completely fills the entire annular space. In the process, the material also closes small gaps or openings between the valve components and between the valve components and the housing parts 5, 9. On the one hand, this results in complete sealing of the annular space and hence also of the through flow channel 15 relative to the housing 3. By virtue of the virtually complete closure of the annular space, the material cannot be extruded at any point, even if the pressure in the material is well above the yield point thereof. On the other hand, the sealing body 27 under pressure simultaneously produces a radial preload on the valve seat elements 17 and guide elements 23. Since the valve seat elements 17, in particular, consist of a hard material which can accept only relatively small tensile stresses but high compressive stresses without being destroyed, the level of the preload must be chosen to be at least such that, at a given maximum pressure for the fluid in the element concerned, only (azimuthal or tangential) compressive stresses below the point at which destruction of the element would occur are produced. For the sake of safety, a sufficient safety margin will, of course, be allowed in practice. However, since it is advisable, for reasons of leaktightness, for the chosen pressure in the sealing body 27 to be higher than the pressure of the fluid in order to ensure the leaktightness of the valve 1, it is at any event certain in this case that the maximum tensile stresses that arise will be below the destruction limit.

This preload also reduces the tensile stresses which are exerted on the seat surface 25 of the valve seat element 17 by the pressure of the ball 19 when the valve is closed. Since hard materials such as sapphire, ruby or ceramic materials are very strong in compression, the preload pressure chosen will not only be high enough to compensate for the pressure of the fluid in the through flow channel 15 but also, in addition, for the radial forces produced by the pressure of the switching element 19 on the valve seat, forces which would lead to expansion of the valve seat element and hence to the destruction of the latter owing to the azimuthal or tangential tensile stresses which would arise.

Metals or metal alloys that are strong in tension, especially stainless steel or titanium alloys, are suitable materials for the housing 3 or housing parts 5, 9.

A valve 1 designed in this way thus has the advantage that the disadvantageous mechanical properties of materials for the valve components, such as sapphire, ruby or ceramic, which, although having a desired high hardness and compressive strength, have only a low tensile strength, and the disadvantageous properties of the material for the sealing element or elements, e.g. thermoplastic materials such as PEEK, which, on the one hand, must be sufficiently flexible to have a sealing action but, on the other hand, would be destroyed by high pressures (without being enclosed on all sides), are compensated.

Since the sealing of the valve 1 by means of the annular sealing body 27 requires only a small annular cross section (i.e. a small wall thickness of the sealing body 7), a very high pressure can be produced in the sealing body 27 with a relatively small force, which is exerted on the correspondingly small end face of the sealing body 27 by means of the second housing part 9.

Instead of producing the preload on the sealing body 27 by mounting (preferably screwing the second housing part 9 to the first housing part 5), it is also (or additionally) possible to deform the wall of the hollow-cylindrical region of the first housing part 5 plastically in the region of the sealing body 27 in such a way that the volume of the annular space in which the sealing body 27 is located is reduced and, accordingly, the desired pressure builds up in the sealing body 27. The deformation of the wall can be accomplished by crimping the metallic wall, for example.

Of course, a whole series of variants of the embodiment illustrated are possible. For example, the seat element 17 can be formed integrally with the guide element 23. In the case of a dual or multiple check valves, the stop for the switching element or ball 19 can be formed by the respective seat element 17 that follows it (in the direction of flow) or is arranged above it. In the case of the last valve unit in the direction of flow, the stop can be formed by the second housing part 9. In this case, the housing part 5 can also be formed integrally with the guide element and extend directly or at least sufficiently into the vicinity of the seat element concerned.

In the case of the illustrative embodiment shown in FIG. 1, there is a free space between the second housing part 9 and the uppermost guide element 23 (i.e. the guide element axially adjacent to the second housing part 9), said space acting as a dead volume 29. Since dead volumes are unwanted in certain applications, the guide element 23 axially adjacent to the second housing part 9 can also be acted upon by the inward-directed end of the second housing part 9, thus minimizing or completely eliminating the dead volume 29. For this purpose, the second housing part 9 can be of correspondingly thicker design (than illustrated in FIG. 1) or can be embodied so that it can be screwed further into the first housing part 5 by means of a thread provided over a greater axial length in the first housing part 5. During the assembly of the valve 1, the second housing part 9 is then screwed into the first housing part until it impinges upon the adjacent guide element 23. At the same time, the sealing body 27 is, of course, also compressed.

According to another embodiment, the outer wall of the housing (in the variant illustrated in FIG. 1, the wall of the first housing part 5) of the valve, which delimits the fully enclosed space in which the sealing body is located, can be designed in such a way that it is elastically or plastically deformable in the entire bounding region or in a part thereof. This property of the housing in the region of this wall is preferably such that, above a predetermined pressure, the volume overall is held constant, despite a further reduction in the size of the space in the region of impingement by the second housing part (in the variant illustrated in FIG. 1 this is housing part 9), by virtue of the fact that the wall is plastically deformed in a corresponding manner at some other point or in some other region. In the embodiment illustrated in FIG. 1, for example, the material and geometry of the wall delimiting the annular space can be such that the wall "bulges" in a defined manner (and in a desired manner) in this region. In this way, it is possible to ensure that the pressure in the sealing body is held (approximately) constant at a predetermined value from a certain threshold. Even if it is not possible to keep the volume of the fully enclosed space and the pressure in the sealing body precisely constant from a predetermined threshold, it is at least possible to ensure by this means that, from a certain threshold, the rise in pressure is less than in the case of a wall without the property of plastic deformability.

In such an embodiment, the second housing part 9 illustrated in FIG. 1, can, for example, be screwed into the first housing part 5 until its end impinges upon the guide element 23 concerned and fixes it in the housing. Thus, as the second housing part 9 is screwed into the first housing part 5, the annular extension 9a of the second housing part does, admittedly, continue to effect a reduction in the volume of the fully enclosed space (of the annular space in the embodiment illustrated in FIG. 1) from a certain position and hence from a certain pressure in the sealing body 27, but this no longer reduces the total volume of the fully enclosed space, or does not do so to the same extent, since the wall of the housing 3 or of the first housing part 5 is deformed and produces an increase in volume in this region.

In this way, the dead volume between the second housing part 9 and the guide element 23 can be eliminated without production tolerances leading to unacceptable rises in pressure in the sealing body 27.

Although the invention has been explained above only with reference to the check valve illustrated in FIG. 1, the invention also relates to all possible embodiments of valves in which the manner according to the invention of sealing and preloading the components of a valve unit of any desired design is employed. For example, the switching element of a switching valve according to the invention can also be designed in such a way that it can be moved actively (manually or by a controllable actuating unit) between two or more operating positions.

What is claimed is:

1. A switching valve to control a fluid subject to high pressure, the switching valve comprising:
   (a) at least one valve unit, which includes a valve seat element and a switching element guided movably in a guide element, wherein the valve seat element and the switching element interact to provide a switching valve function;
   (b) wherein the valve seat element and the guide element are provided in a housing and wherein the valve seat element, the guide element and the housing form a through flow channel for the fluid to be controlled; and
   (c) an elastically and/or plastically deformable sealing body in a fully enclosed space between an inner wall of the housing and an outer walls of the valve seat element and of the guide element, the sealing body being subject to a predetermined pressure and thus sealing off the through flow channel and subjecting the valve seat element and the guide element to a radially inward-directed preload pressure.

2. The switching valve according to claim 1, in which the pressure in the sealing body is greater than a maximum pressure of the fluid to be controlled in the through flow channel.

3. The switching valve according to claim 1, in which the housing is of at least a two-part design, in that a receiving recess for the valve seat element, the guide element and the sealing body is provided in a first housing part, and in that a second housing part is connected to the first housing part where the second housing part subjects the sealing body to the predetermined pressure.

4. The switching valve according to claim 2, in which the housing is of at least a two-part design, in that a receiving recess for the valve seat element, the guide element and the sealing body is provided in a first housing part, and in that a second housing part is connected to the first housing part that subjects the sealing body to the predetermined pressure.

5. The switching valve according to claim 3, in which the receiving recess in the first housing part is cylindrical, and in that the valve seat element and the guide element have an axially flush cylindrical outer wall.

6. The switching valve according to claim 3, in which the second housing part is connected detachably to the first housing part by screwing, and in that the second housing part has an annular extension, which engages in an annular space that subjects the sealing body to the predetermined pressure and closes the space.

7. The switching valve according to claim 1, in which the guide element has a recess to receive the switching element, in which the recess is configured so that an axial movement of the switching element into an OPEN position of the valve, which takes place in a direction away from the valve seat, is limited.

8. The switching valve according to claim 3, in which, the predetermined pressure causes the first housing part to include a plastically deformed wall where the plastically deformed wall delimits the fully enclosed space.

9. The switching valve according to claim 1, in which the sealing body surrounds at least one further valve unit, which is in alignment with the first valve unit and which forms at least one further through flow channel that is connected fluidically in series with the through flow channel of the first valve unit.

10. The switching valve according to claim 9, in which the at least one further valve unit is of identical design to the first valve unit and in that the valve units are in direct axial contact with one another.

11. The switching valve according to claim 1, in which the switching element is a material selected from the group consisting of ruby, sapphire, and ceramic.

12. The switching valve according to claim 1, in which the switching element is a ceramic material selected from the group consisting of $AlO_2$ and $ZrO_2$.

13. The switching valve according to claim 1, in which the valve seat element is a material selected from the group consisting of ruby, sapphire, and ceramic material.

14. The switching valve according to claim 1, in which the valve seat element is a ceramic material selected from the group consisting of $AlO_2$ and $ZrO_2$.

15. The switching valve according to claim 1, in which the housing includes a metallic material selected from the group consisting of stainless steel and titanium alloy.

16. The switching valve according to claim 1, in which the sealing body comprises a thermoplastic.

17. The switching valve according to claim 16, in which the thermoplastic includes a polyether ether ketone (PEEK).

18. The switching valve according claim 1, in which the valve is configured to be a check valve and in which the switching element is a ball.

19. The switching valve according to claim 3, in which an outer wall of the first housing part is configured to be elastically or plastically deformable in at least one partial region to delimit the fully enclosed space.

* * * * *

UNITED STATES PATENT AND TRADEMARK OFFICE
CERTIFICATE OF CORRECTION

PATENT NO. : 9,133,944 B2  
APPLICATION NO. : 13/705657  
DATED : September 15, 2015  
INVENTOR(S) : Michael Hackel Page 1 of 1

It is certified that error appears in the above-identified patent and that said Letters Patent is hereby corrected as shown below:

In the Claims

Column 11, line 33 (approx.), In Claim 8, delete "in which," and insert -- in which --, therefor.

Column 12, line 16 (approx.), In Claim 12, delete "AlO2 and ZrO2." and insert -- $AlO_2$ and $ZrO_2$. --, therefor.

Column 12, line 22 (approx.), In Claim 14, delete "AlO2 and ZrO2." and insert -- $AlO_2$ and $ZrO_2$. --, therefor.

Column 12, line 30 (approx.), In Claim 18, delete "according" and insert -- according to --, therefor.

Signed and Sealed this  
Twenty-third Day of August, 2016

Michelle K. Lee  
*Director of the United States Patent and Trademark Office*